(12) United States Patent
Roeder et al.

(10) Patent No.: US 8,740,972 B2
(45) Date of Patent: Jun. 3, 2014

(54) MEDICAL DEVICE WITH ANCHOR MEMBERS

(75) Inventors: Blayne A. Roeder, Bloomington, IN (US); Alan R. Leewood, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/517,954

(22) PCT Filed: Dec. 9, 2010

(86) PCT No.: PCT/US2010/059680
§ 371 (c)(1),
(2), (4) Date: Jun. 20, 2012

(87) PCT Pub. No.: WO2011/087644
PCT Pub. Date: Jul. 21, 2011

(65) Prior Publication Data
US 2012/0259408 A1      Oct. 11, 2012

Related U.S. Application Data

(60) Provisional application No. 61/289,257, filed on Dec. 22, 2009.

(51) Int. Cl.
*A61F 2/06* (2013.01)
(52) U.S. Cl.
USPC .................................. 623/1.36; 623/1.15
(58) Field of Classification Search
USPC ............................................. 623/1.36, 1.15
See application file for complete search history.

(56) References Cited

U.S. PATENT DOCUMENTS

| | | | |
|---|---|---|---|
| 5,397,355 | A | 3/1995 | Marin et al. |
| 2003/0220683 | A1 | 11/2003 | Minasian et al. |
| 2009/0082841 | A1 | 3/2009 | Zacharias et al. |

FOREIGN PATENT DOCUMENTS

| | | |
|---|---|---|
| EP | 0 974 314 A2 | 1/2000 |
| EP | 1 810 642 A2 | 7/2007 |
| EP | 2 110 102 A1 | 10/2009 |
| WO | WO 00/64355 A1 | 11/2000 |
| WO | WO 2009/042789 A2 | 4/2009 |
| WO | WO 2010/126889 A1 | 11/2010 |

OTHER PUBLICATIONS

International Search Report for International Application No. PCT/US2010/059680, dated Apr. 1, 2011, 3 pages.

*Primary Examiner* — Thomas J Sweet
*Assistant Examiner* — Matthew Schall
(74) *Attorney, Agent, or Firm* — Brinks Gilson & Lione; Ryan L. Marshall

(57) ABSTRACT

An implantable medical support frame (104) having a central longitudinally extending axis is expandable from a collapsed configuration having a first diameter to an expanded configuration having a second diameter. The frame also includes an anchoring mechanism with an elongate member (110). At least a portion of the elongate member is slidably disposed within a retaining structure when the frame is in the collapsed configuration. When the frame expands from the collapsed configuration to the expanded configuration, a portion of the elongate member is advanced out of the retaining structure such that the portion of the elongate member protrudes radially outward of the frame at an angle to the axis, thereby forming an anchor. A length of the protruding portion of the anchor increases as the frame expands from the collapsed configuration to the expanded configuration.

20 Claims, 11 Drawing Sheets

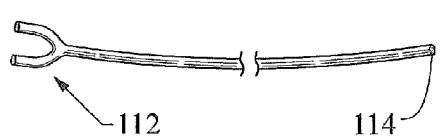
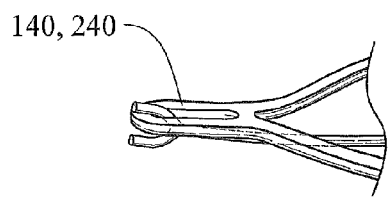
Fig. 3(a)      Fig. 3(b)
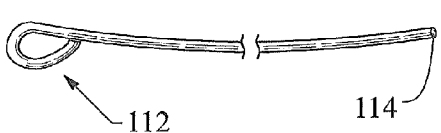
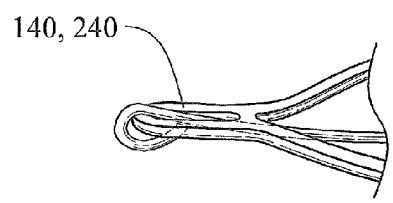
Fig. 4(a)      Fig. 4(b)
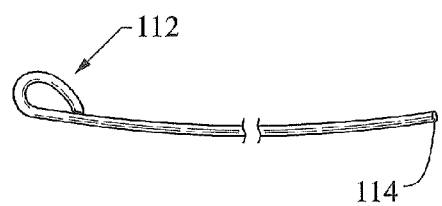
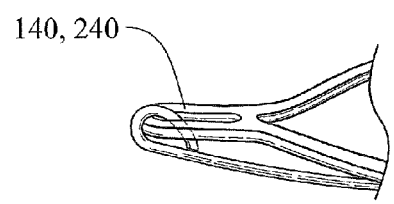
Fig. 5(a)      Fig. 5(b)

US 8,740,972 B2

MEDICAL DEVICE WITH ANCHOR MEMBERS

REFERENCE TO EARLIER FILED APPLICATIONS

This application is a 371 national phase of PCT/US2010/059680, filed Dec. 9, 2010, and claims the benefit under 35 U.S.C. §119(e) of U.S. Provisional Application No. 61/289,257, filed Dec. 22, 2009, the disclosures of which are incorporated, in their entirety, by this reference.

TECHNICAL FIELD

This invention relates to medical devices and, in particular, to prostheses for placement in a body lumen.

BACKGROUND ART

The functional vessels of human and animal bodies such as the esophagus, bile duct, and blood vessels occasionally become damaged or diseased. For example, the aortic wall can weaken, resulting in an aneurysm. Upon further exposure to hemodynamic forces, an aneurysm can rupture.

Endoluminal prostheses, such as stents and stent-grafts, may be used for treating damaged or diseased functional vessels. For example, a stent graft may be used for repairing abdominal and thoracic aortic aneurysms. Such a stent-graft is placed inside the vessel and provides some or all of the functionality of the original, healthy vessel.

One of the challenges of designing and using an endoluminal prosthesis is preventing migration of the prosthesis once it is placed in a body lumen. This challenge is particularly great when the environment in which the prosthesis is placed is subject to a continuous strain, such as by the pulsatile force of blood flow in the vasculature. When an endoluminal prosthesis is used, for example, to repair an aneurysm, migration of the device may result in endoleaks or inadequate exclusion of the aneurysm, and increased risk of aneurysm rupture.

Various devices have been proposed to address migration. For example, a prosthesis may comprise one or more anchor members, such as a barb or hook, that extends radially outward from the prosthesis and is configured to engage surrounding body tissue. Typically, such barbs or hooks may be attached to the prosthesis by, for example, sewing, gluing, wrapping, chemical bonding, welding, brazing, soldering, and the like.

DISCLOSURE OF THE INVENTION

Retractable anchor mechanisms are described which limit or prevent migration of a prosthesis and further facilitate insertion into a delivery system. The embodiments may include any of the following aspects in various combinations and may also include any other aspect described below in the written description or in the attached drawings.

In one aspect, an implantable medical support frame may include a frame having a central longitudinally extending axis. The frame may be expandable from a collapsed or compressed configuration having a first diameter to an expanded configuration having a second diameter, the second diameter being greater than the first diameter. An anchoring mechanism having an elongate member is also included. At least a portion of the elongate member is slidably disposed within a retaining structure when the frame is in the collapsed configuration. When the frame expands from the collapsed configuration to the expanded configuration, a portion of the elongate member is advanced out of the retaining structure such that the portion of the elongate member protrudes radially outward of the frame at an angle to the central axis and forms an anchor. A length of the protruding portion of the anchor increases as the frame expands from the collapsed configuration to the expanded configuration.

In another aspect, the elongate member may have first and second ends. The second end is coupled to the frame, and the first end is free of attachment to the frame. In one embodiment, the second end of the elongate member is fixedly attached to the frame.

The foregoing paragraphs have been provided by way of general introduction, and are not intended to limit the scope of the following claims. The described embodiments will be best understood by reference to the following detailed description taken in conjunction with the accompanying drawings.

BRIEF DESCRIPTION OF THE DRAWINGS

The embodiments may be more fully understood by reading the following description in conjunction with the drawings, in which:

FIG. 3(a) is a side view of an embodiment of an elongate anchor member;

FIG. 3(b) is a plan view of the elongate anchor member of FIG. 3(a) attached to an implantable medical support frame;

FIG. 4(a) is a side view of an embodiment of an elongate anchor member;

FIG. 4(b) is a plan view of the elongate anchor member of FIG. 4(a) attached to an implantable medical support frame;

FIG. 5(a) is a side view of an embodiment of an elongate anchor member;

FIG. 5(b) is a plan view of the elongate anchor member of FIG. 5(a) attached to an implantable medical support frame;

DETAILED DESCRIPTION

Figure 1A:
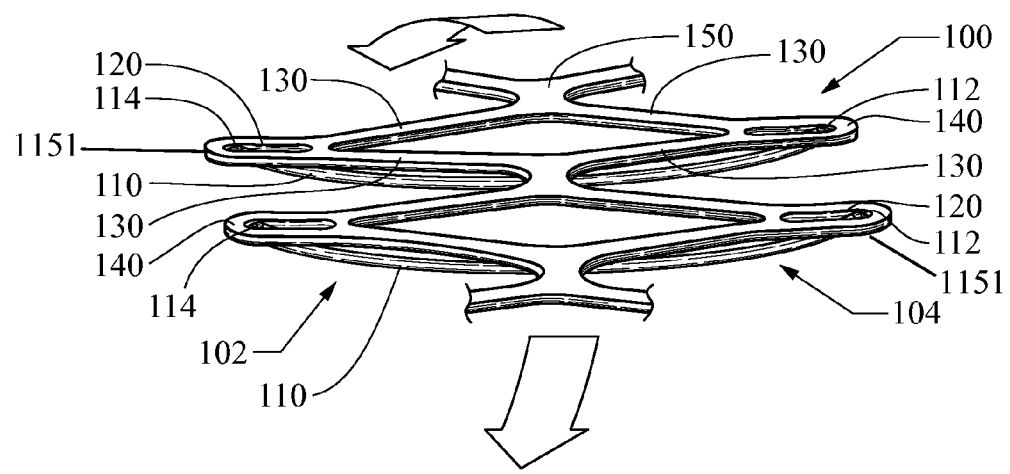
FIG. 1(a) is a plan view of a portion of an embodiment of an implantable medical support frame having a retractable anchor member in a collapsed configuration.
Figure 1B:
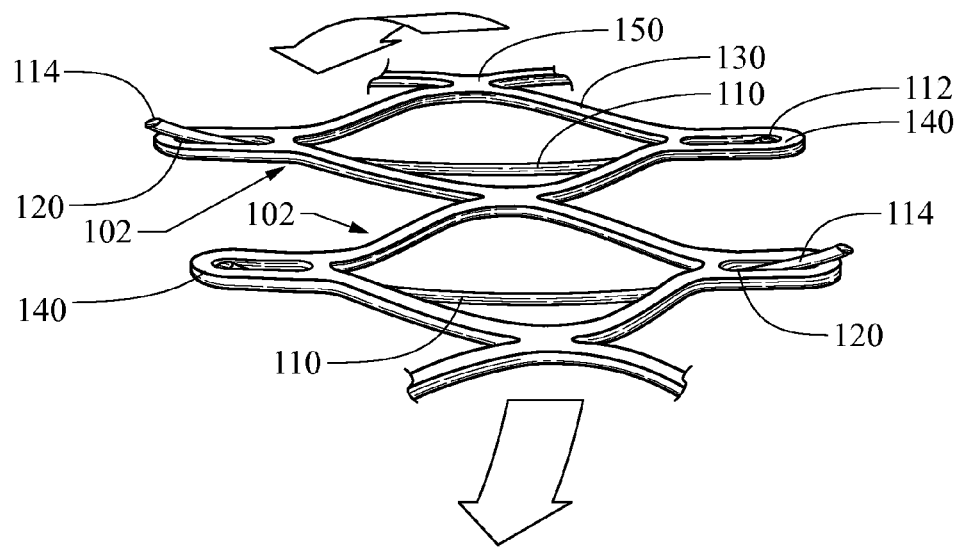
FIG. 1(b) is a plan view of a portion of the embodiment of FIG. 1(a) in a partially expanded configuration.
Figure 1C:
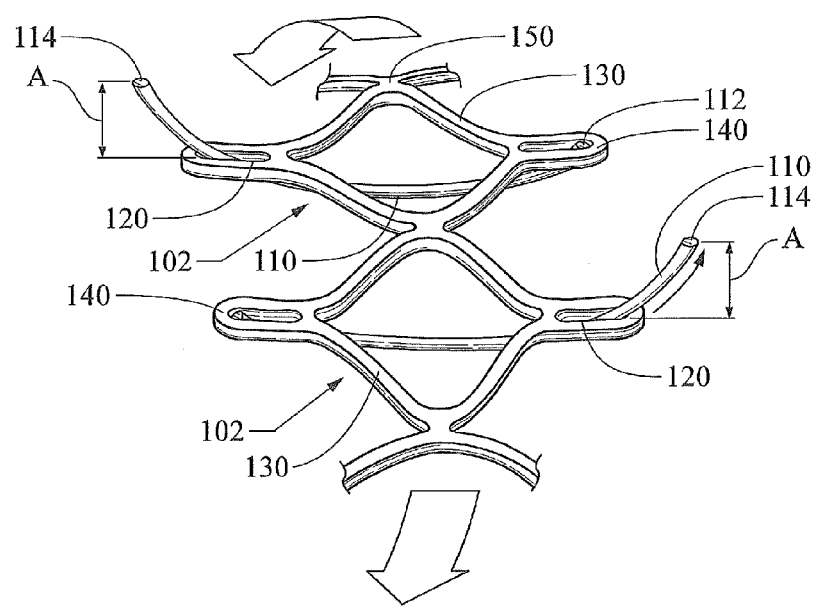
FIG. 1(c) is a plan view of a portion of the embodiment of FIG. 1(a) in a fully expanded configuration.

Referring now to the figures, FIGS. 1(a)-(c) illustrate an embodiment of an endoluminal prosthesis 100 having a retractable anchor member. Throughout this description, like reference numbers refer to like elements in the Figures. As shown in FIG. 1(a), the endoluminal prosthesis 100 includes a radially expandable frame 104 comprising a plurality of strut members 130 connected by bends in an undulating pattern to form a ring-like structure having a substantially cylindrical shape. Various designs may be used for the frame 104. For example, the frame 104 may be made with undulating, serpentine rings interconnected with longitudinal structural members. The frame 104 may be fabricated from a cannula, as disclosed in U.S. Pat. Nos. 6,231,598, and 6,743,252, which are assigned to Cook Inc., the assignee of the present invention and are hereby incorporated by reference in their entirety. The strut members 130 may be made from elastic, super-elastic, or spring-metal alloys such as nitinol, stainless steel, cobalt chromium, nickel titanium, platinum, inconel, or any other suitable material, such that the strut members 130 can compress under force, and when unrestrained will tend to return to the expanded configuration in a spring-like manner. That is, in an embodiment, the frame 104 and the cells 102 are self-expanding. Alternatively, the strut members 130 may be made from a plastically deformable material such as stainless steel or the like that is expandable from a collapsed or compressed configuration to an expanded configuration by a balloon or the like.

The frame 104 also includes one or more anchor retaining structures. The retaining structures may include one or more cells 102. In another embodiment, each cell 102 may be at least partially defined by two pairs of circumferentially adjacent strut members 130 connected by individual bends. More specifically, each cell may be formed from a left and a right upper strut member 130 and a left and a right lower strut member 130. Each of the left and right upper and lower strut members 130 has an inner and an outer end. The outer ends of the left upper and lower strut members 130 are connected by a single bend disposed at a left longitudinal end of the cell 102, such that the left upper and lower strut members 130 extend away from the bend and toward a center of the cell 102. Similarly, the outer ends of the right upper and lower strut members 130 are connected by a single bend disposed at a right longitudinal end of the cell 102, such that the right upper and lower strut members 130 extend away from the bend and toward a center of the cell 102. The inner ends of the left and right upper strut members 130 are connected at an upper connecting member 150 and the inner ends of the left and right lower strut members 130 are connected at a lower connecting member 150. Each cell 102 also includes an anchor attachment portion 140 attached to one of the bends, and an anchor deployment portion 120 attached to the other bend.

The strut members 130 of the frame 104 and the cells 102 are configured to flex between a collapsed configuration, depicted in FIG. 1(a), and an expanded configuration, depicted in FIG. 1(c). When the frame 104 and the cells 102 are the collapsed configuration, the left upper strut member 130 and the left lower strut member 130 are substantially adjacent to each other. For example, the left upper strut member 130 and the left lower strut member 130 may be substantially parallel or form an acute angle with one another. Similarly, the right upper strut member 130 and the right lower strut member 130 are substantially adjacent to each other such that the upper and lower right strut members 130 are substantially parallel or form an acute angle.

As shown in FIG. 1(b), as the frame 104 and the cells 102 begin to expand in the radially outward direction, the upper and lower strut members 130 begin to flex away from each other such that the angle between the upper left and lower left, and the angle between the upper right and lower right strut members 130 increases. Because the strut members 130 have a fixed length that does not stretch during the expansion process, as the angle between the upper and lower struts 130 increases it causes a length of the cells 102 to increase in the circumferential direction and decrease in the axial/longitudinal direction. Note that the collapsed configuration need not correspond to a maximally collapsed configuration, and may refer to any intermediate configuration between the maximum collapsed and expanded states, provided that the outer diameter of the frame 104 is smaller in the collapsed configuration than in the expanded configuration. Similarly, the expanded configuration need not correspond to a maximally expanded configuration and may refer to any intermediate configuration between the maximum expanded and collapsed states, provided that the outer diameter of the frame 104 is larger in the expanded configuration than in the collapsed configuration.

It should be understood that while the strut members 130 are depicted as being straight, they are not limited thereto, and the strut members may have any curvilinear shape along their length to distribute bending forces and like during use. It should also be understood that while FIG. 1(a) depicts the portion of the frame 104 corresponding to the cells 102, in one embodiment the frame 104 may be wholly comprised of interconnected cells 102 that extend around a circumference of the frame 104. In other embodiments, the frame 104 may contain some portions comprising cells 102 and other portions comprising strut members 130 arranged in other radially expandable patterns, for example and without limitation, zig-zag, serpentine, and sinusoidal patterns.

An elongate anchor member 110 is attached to the anchor attachment portion 140 of the retaining structure at an anchor end 112. The anchor attachment portion 140 may be formed as a lobe attached to a bend connecting the upper and lower right or left strut members 130, and may include an aperture to receive the anchor end 112 of the elongate anchor member 110. The elongate anchor member 110 also includes an engagement end 114 that is configured to extend through an anchor deployment portion 120. The anchor deployment portion 120 may be shaped as a lobe and is attached to the bend opposite the bend connected to the anchor attachment portion 140.

The engagement end 114 may be shaped to fixedly engage and penetrate into a wall of a body lumen or an inner surface of stent graft, such as a modular stent-graft endoluminal prosthesis, for example, the Zenith Endovascular Grafts sold by Cook Incorporated, the assignee of the present application. Exemplary shapes of the engagement end 114 include, but are not limited to, a conical point, a bevel, and a multi faced cutting surface or the like. The engagement end 114 may also be shaped to withstand repetitive loading experienced by anchor members in vivo, as described in U.S. Provisional Patent Application Ser. No. 61/138,355, which is assigned to Cook, Inc., the assignee of the present application, and incorporated herein in its entirety.

The anchor member 110 may extend from the anchor attachment portion 140 to the anchor deployment portion 120 along a radially inner surface of the cell 102. In this way, the retaining structure prevents the portion of the anchor member 110 that is not designed to engage a vessel wall or endoluminal prosthesis from potentially interfering with the frame 104 and vessel wall/outer stent-graft interface. The anchor member 110 may be made from any elastic, super-elastic, or spring-metal alloys such as nitinol, stainless steel, cobalt chromium, nickel titanium, platinum, inconel, or any other material, such that the anchor member 110 will tend to return to its predetermined shape when unrestrained. In one embodiment, the anchor member 110 may have a radially outwardly arching shape that biases the engagement end 114 in a radially outward direction, thereby increasing apposition and penetration in to the vessel wall or stent graft. In another embodiment, the anchor member 110 may be substantially straight along its length. In the substantially straight embodiment, the anchor deployment portion 120 may include a deflecting member 1151 that is designed to slidingly engage and deflect the engagement end 114 in the radially outward direction. The deflecting member may be a radially outward curved or angled surface (see also FIGS. 10(a), 10(b), 11(a), 11(b), 12(a), and 12(b) discussed below).

As shown in FIG. 1(a), the anchor member 110 may have a length that is substantially equal to a distance between the anchor attachment portion 140 to the anchor deployment portion 120 when the cell 102 is in a fully collapsed configuration. In this way, when the cell 102 is in the fully collapsed configuration, the engagement end 114 of the anchor member 110 is disposed radially within the cell 102 and does not protrude beyond a radially external surface of the frame 104. Thus, when each of the frame 104 and the cell 102 is in its completely collapsed configuration, the retaining structure prevents the engagement end 114 of the anchor member 110 from potentially engaging or interfering with a retention sheath of a delivery system during loading or deployment.

In one embodiment, the anchor end 114 of the elongate anchor member 110 may be fixedly attached to the anchor attachment portion 140 by welding, soldering, crimping, bonding, or any other suitable method. Alternatively, as shown in FIGS. 3-5, the anchor end 114 of the elongate anchor member 110 may be configured to mechanically couple to the anchor attachment portion 140 in a non-fixed manner to help reduce stress concentrations at the bond location between the elongate anchor member 110 and the anchor attachment portion 140. The anchor end 114 may have a bifurcated shape designed to be inserted into an aperture disposed in the anchor attachment portion 140 and receive a surface thereof, as shown in FIGS. 3(a) and (b). As shown in FIGS. 4(a)-5(b), the elongate anchor member 110 may be formed from a continuous piece of metallic wire that is inserted through an aperture in the anchor attachment portion 140 and looped around an outer surface thereof, thereby coupling the elongate anchor member 110 to the anchor attachment portion 140.

In operation, as the strut members 130 of the frame 104 and the cells 102 expand from the collapsed configuration shown in FIG. 1(a), to the fully expanded configuration shown in FIG. 1(c), the anchor end 112 is held in place relative to the anchor attachment portion 140. As the longitudinal distance between the anchor attachment portion 140 and the anchor deployment portion 120 decreases due to the expansion of the cell 102 in the circumferential direction, the engagement end 114 is forced outward through the anchor deployment portion 120. Upon complete deployment, the deployment portion 120 of the elongate anchor member 110, including the engagement end 114, extends radially outward of the external surface of the retaining structure by a distance A. The distance A may be between about one to two or about one to four times the thickness of the elongate anchor member 110. For example and without limitation, the elongate anchor member 110 may have a thickness of between about 0.2 mm and 0.6 mm. Accordingly, the distance A may be approximately 0.2 mm to approximately 2.4 mm. The distance A may be the same or different for each elongate anchor member 110 and each cell 102 to provide a desired tacking characteristic. Further, although the anchor attachment portions 140, the anchor deployment portions 120, and the elongate anchor members 110 are depicted with alternating orientation for each cell 102, they are not limited thereto, and other configurations are contemplated.

It should be understood that the distance A may be greater or less than this range, so long as the portion of the elongate anchor member 110 is sufficiently long to provide adequate penetration into the surrounding vessel or stent-graft/desired structure and prevent migration of the endoluminal prosthesis 100. Thus, as the frame 104 and the cells 102 are expanded, either through self-expansion or by a balloon, etc., the elongate anchor member 110 moves from a retracted position, in which the engagement end 114 of the anchor member 110 is disposed radially within the cell 102 and does not protrude beyond the external surface of the frame 104, to a deployed position, in which the engagement end 114 is disposed radially outward of the external surface of the frame 104 to form an anchor or barb. Because the engagement end 104 is contained within the cells 102 when the frame 104 is in the initial collapsed state, the external surface of the endoluminal prosthesis 100 in the collapsed state is free of protrusions that may interfere with a retention sheath during loading or deployment.

This "barbless" profile in the collapsed configuration provides significant benefits over conventional barbed stents or stent grafts. For example, the endoluminal prosthesis 100 can be loaded into a delivery system in the same manner as a conventional barbless stent or stent-graft without potentially scarring or shaving the inner surface of a retention sheath or the like. The endoluminal prosthesis 100 can also be advanced through a modular prosthesis or a body lumen in an exposed, uncovered condition without the risk of inadvertent or unwanted snagging, scarring, or interference experienced with conventional barbed stents, stent-grafts and the like. Furthermore, because the barbs retract within the cells 102, the endoluminal prosthesis 100 is capable of being "resheathed" during deployment. The resheathing process typically involves advancing a retention sheath of a delivery system in the distal direction over a partially deployed prosthesis. In conventional barbed prostheses, once the barbed portion is deployed, the barbs assume their outwardly protruding configuration, thus preventing the sheath from being advanced beyond the exposed/deployed barbs. In contrast, because the barb/anchor portion of the elongate anchor member 110 of this embodiment automatically retracts within the retaining structure as the frame 104 is collapsed, it is possible to resheath the prosthesis by advancing the retention sheath distally over the partially deployed endoluminal prosthesis 100 and compressing the frame 104.

Figure 2A:
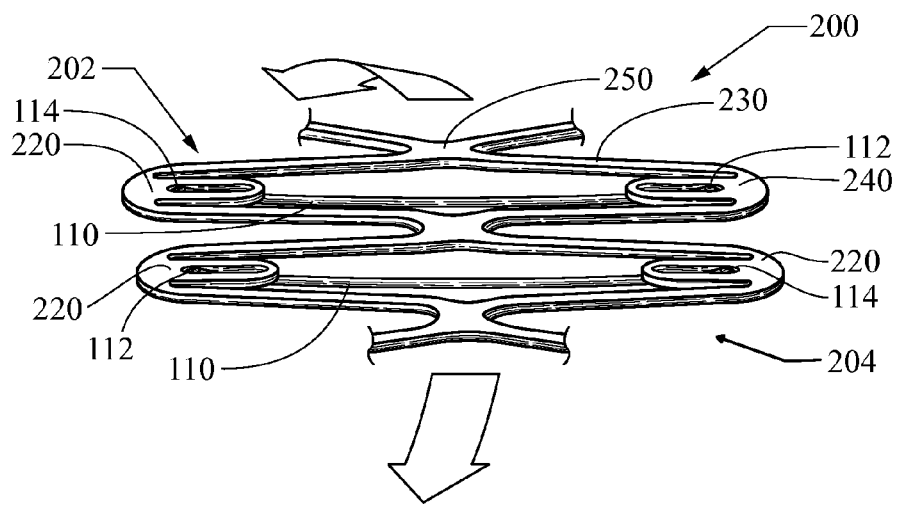
FIG. 2(a) is a plan view of a portion of another embodiment of an implantable medical support frame having a retractable anchor member in a collapsed configuration.
Figure 2B:
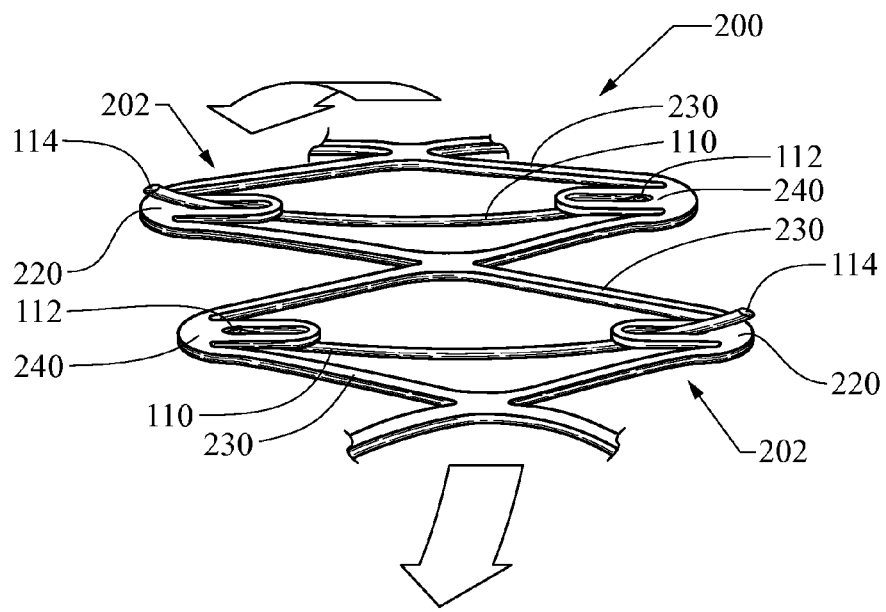
FIG. 2(b) is a plan view of a portion of the embodiment of FIG. 2(a) in a partially expanded configuration.
Figure 2C:
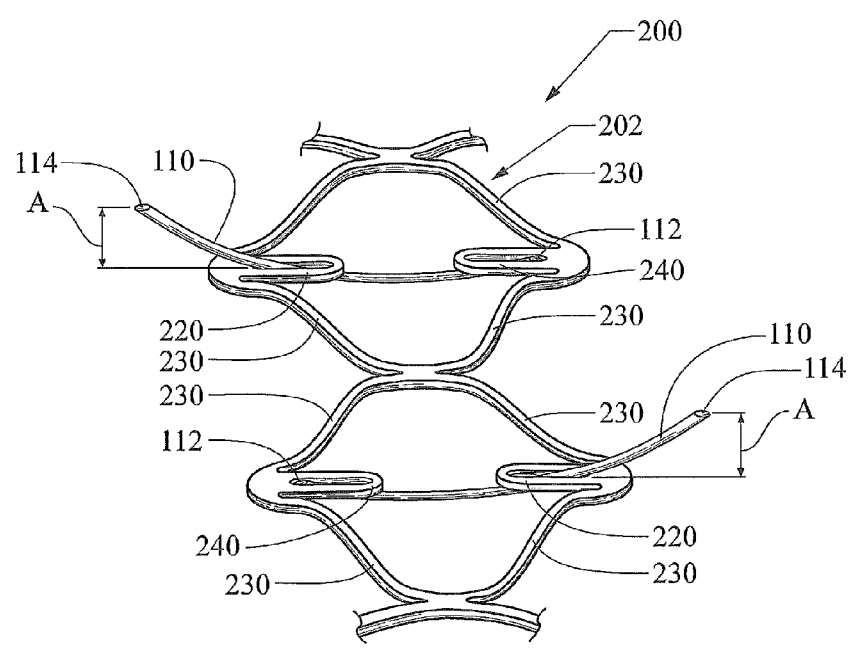
FIG. 2(c) is a plan view of a portion of the embodiment of FIG. 2(a) in a fully expanded configuration.

FIGS. 2(a)-(c) illustrate another embodiment of the endoluminal prosthesis 200, in which the anchor attachment portion 140 and the anchor deployment portion 120 are attached to an inner surface of the bends connecting the upper and lower pairs of strut members 130. The embodiment of FIGS. 2(a)-(c) includes a radially expandable frame 204 comprising a plurality of strut members 230 connected by bends in an undulating pattern to form a ring-like structure having a substantially cylindrical shape. As with the embodiment of FIGS. 1(a)-(c), various designs may be used for the frame 204. For example, the frame 204 may be made of undulating, serpentine rings interconnected with longitudinal connecting members. The strut members 230 are made from elastic, super-elastic, or spring-metal alloys as described above in connection with embodiment of FIGS. 1(a)-(c). The frame 204 may be self or balloon expandable.

The frame 204 also includes one or more retaining structures. The retaining structures may include one or more cells 202. In one embodiment, each cell 202 may be at least partially defined by two pairs of circumferentially adjacent strut members 230 connected by individual bends. More specifically, each cell may be formed from a left and a right upper strut member 230 and a left and a right lower strut member 230. Each of the left and right upper and lower strut members 230 has an inner and an outer end. The outer ends of the left upper and lower strut members 230 are connected by a single bend disposed at left longitudinal end of the cell 202, such that the left upper and lower strut members 230 extend away from the bend and toward a center of the cell 202. Similarly, the outer ends of the right upper and lower strut members 230 are connected by a single bend disposed at a right longitudinal end of the cell 202, such that the right upper and lower strut members 230 extend away from the bend and toward a center of the cell 202. The inner ends of the left and right upper strut members 230 are connected at an upper connecting member 250 and the inner ends of the left and right lower strut members are connected at a lower connecting member 250. Each cell 202 also includes an anchor attachment portion 240 attached to an inner surface one of the bends, and an anchor deployment portion 220 attached to an external surface of the other bend. The anchor attachment portion 240 and the anchor deployment portion 220 extend from the respective bends toward a midpoint of the cell 202.

It should be understood that while the strut members 230 are depicted as being straight, they are not limited thereto, and the strut members may have any curvilinear shape along their length to distribute bending forces and the like during use. The strut members may also have varied widths along their length. It should also be understood that while FIGS. 2(a)-(c) depict the portion of the frame 204 corresponding to the cells 202, in one embodiment, the frame 204 may be wholly comprised of interconnected cells 202 that extend around a circumference of the frame 204. In other embodiments, the frame 204 may contain some portions utilizing the cells 202 and other portions utilizing strut members 230 arranged in other radially expandable patterns, for example and without limitation, zigzag, serpentine, and sinusoidal patterns.

An elongate anchor member 110 is attached to the anchor attachment portion 240 of the retaining structure at an anchor end 112. The anchor attachment portion 240 may be formed as a lobe attached to a bend connecting the upper and lower right or left strut members 230, and may include an aperture to receive the anchor end 112 of the elongate anchor member 110. The elongate anchor member 110 also includes an engagement end 114 that is configured to extend through an anchor deployment portion 220. The anchor deployment portion 220 may be shaped as the anchor deployment portion 120 described above in connection with embodiment of FIGS. 1(a)-(c). As with embodiment of FIGS. 1(a)-(c), the anchor member 110 extends from the anchor attachment portion 240 to the anchor deployment portion 220 along a radially inner surface of the cell 202. The elongate anchor member 110 has a length that is substantially equal to a distance between the anchor attachment portion 240 to the anchor extruding portion 220 when the cell 202 is in a fully collapsed configuration. The anchor end 114 may be attached to the anchor attachment portion 240 in the manners described above in connection with embodiment of FIGS. 1(a)-(c).

The frame 204, the cells 202, and the elongate anchor member 110 in the endoluminal prosthesis 200 function in substantially the same way as the embodiment of FIGS. 1(a)-(c), and therefore their operation will not be described again.

FIGS. 6-12 illustrate alternative embodiments of the endoluminal prosthesis. As shown in FIGS. 6(a)-7(b), the frame may include cells 720 and 722 having anchor attachment portions 640 disposed at opposite longitudinal ends thereof. The cells 720, 722 may or may not be circumferentially adjacent one another. Each anchor attachment portion 640 includes an aperture 642. An elongate anchor member 710 is threaded through the apertures 642 of the cells 720, 722 and bends around an outer edge of the respective anchor attachment portions 640. In this way, the elongate anchor member 710 is fixed to each of the anchor attachment portions 640 and prevents the elongate anchor member 710 from moving relative to the anchor attachment portion 640 in the longitudinal direction as the frame 604 expands from the collapsed configuration (FIG. 6(a)) to the expanded configuration (FIG. 7(a)).

Figure 6A:
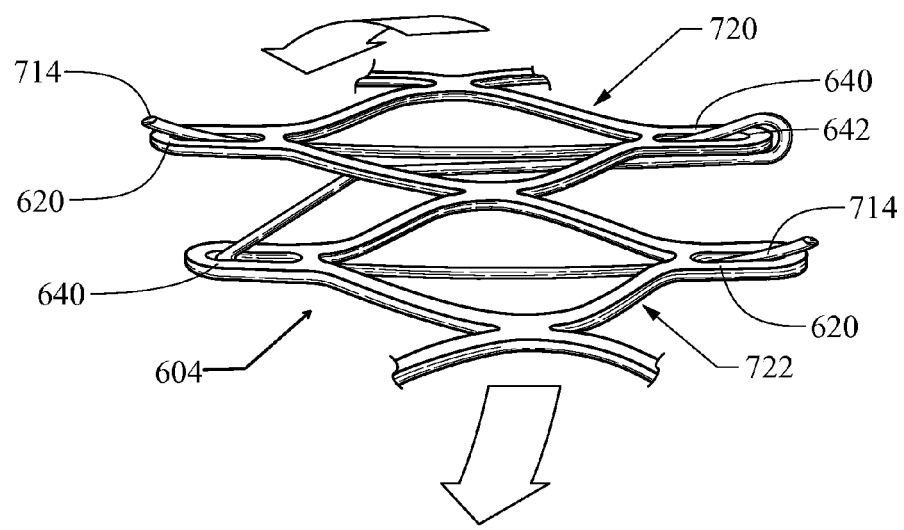
FIG. 6(a) is a plan view of the medical support frame of FIGS. 1(a)-(c) utilizing another embodiment of an elongate anchor member in a partially collapsed configuration.
Figure 6B:
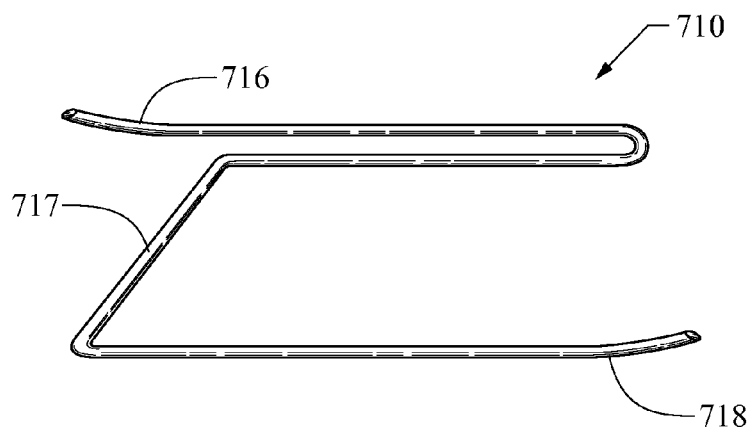
FIG. 6(b) is a plan view of the elongate anchor member of FIG. 6(a) in the partially collapsed configuration.
Figure 7A:
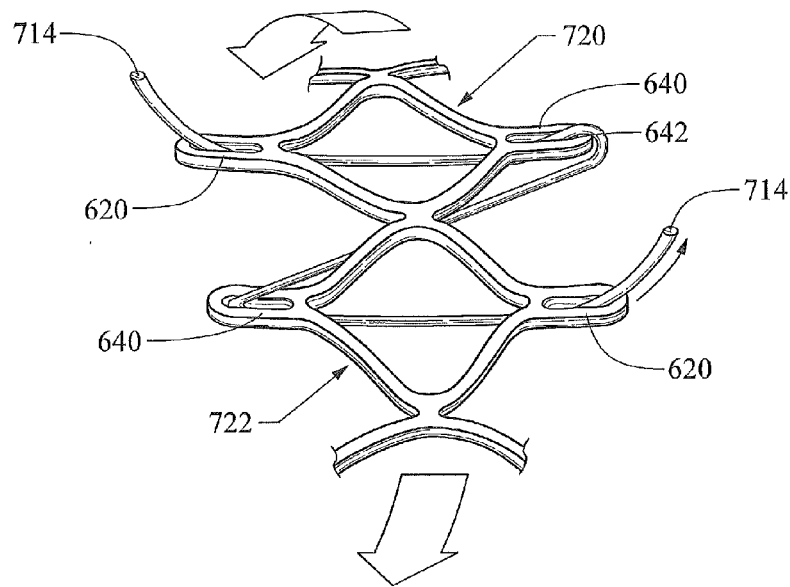
FIG. 7(a) is a plan view of the embodiment of FIG. 6(a) in a fully expanded configuration.
Figure 7B:
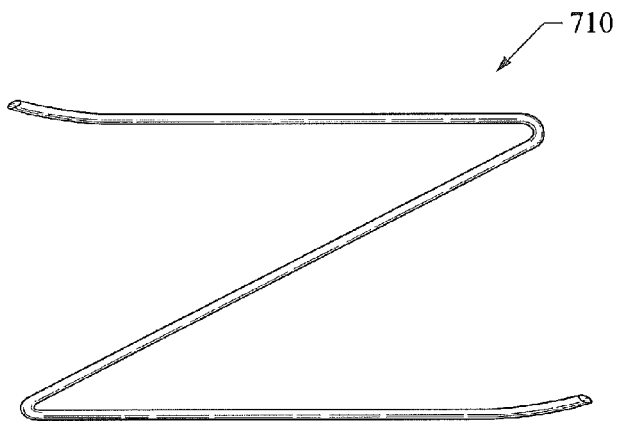
FIG. 7(b) is a plan view of the elongate anchor member of FIG. 7(a) in the fully expanded configuration.

As shown in FIG. 6(b), the elongate anchor member 710 has first and second portions 716, 718 that are configured substantially the same as the elongate member 110 described above in connection with the embodiments of FIGS. 1(a)-(c) and 2(a)-(c). The first and second portions 716, 718 are connected by a member 717 which is expandable along the circumferential direction of the prosthesis. Member 717 includes two straight portions connected at an angle by a bend disposed at a midsection thereof. As the cells 720, 722 expand from the collapsed to the expanded configuration (FIGS. 6(b) and 7(b)), the expandable member 717 straightens, thereby expanding the elongate anchor member 710. In operation, as the frame 104 is expanded, a distance between the anchor attachment portions 640 and the anchor deployment portions 620 decreases, thereby forcing the engagement ends 714 of the elongate anchor member 710 through the anchor deployment portions 620 in the radially outward direction, as described above in connection with FIGS. 1(a)-2(c).

As shown in FIGS. 8(a)-9(b), cells 920 and 922 have anchor attachment portions 840 disposed at the same longitudinal ends. The cells 920, 922 may or may not be circumferentially adjacent one another. Each anchor attachment portion 840 includes an aperture 842. An elongate anchor member 810 includes a coupling member 816 that is inserted into the apertures 842 of the cells 920, 922 to attach the elongate anchor member 810 to each of the anchor attachment portions 840 and prevent the elongate anchor member 810 from moving relative to the anchor attachment portion 840 in the longitudinal direction as the frame 804 expands from the collapsed configuration (FIG. 8(a)) to the expanded configuration (FIG. 9(a)).

Figure 8A:
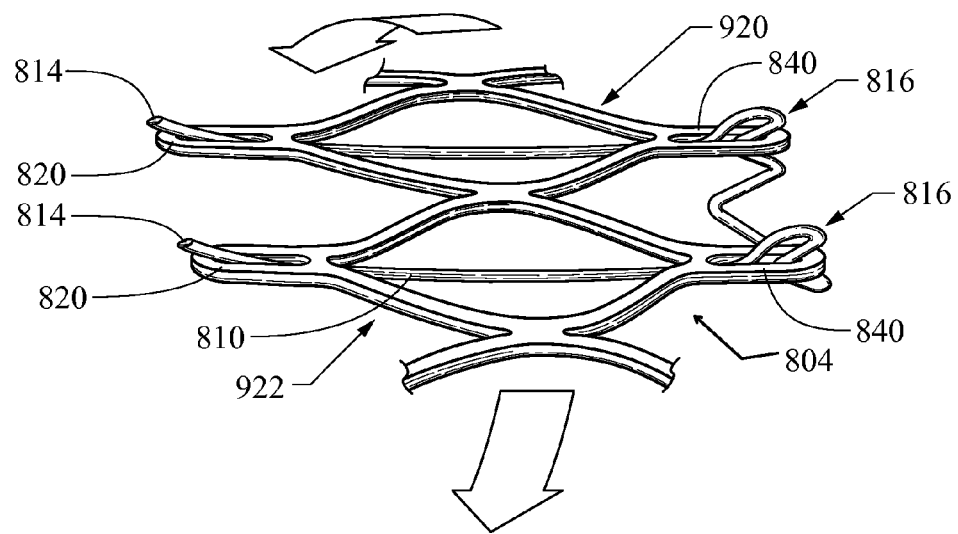
FIG. 8(a) is a plan view of the medical support frame of FIGS. 1(a)-(c) utilizing another embodiment of an elongate anchor member in a partially collapsed configuration.
Figure 8B:
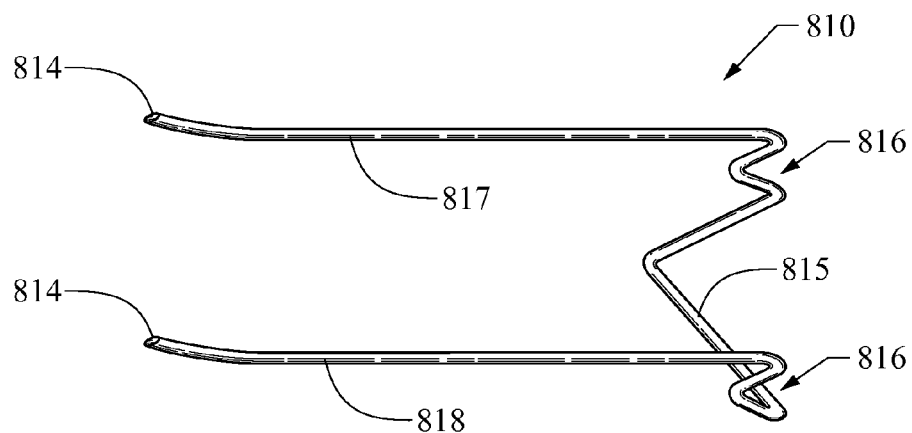
FIG. 8(b) is a plan view of the elongate anchor member of FIG. 8(a) in the partially collapsed configuration.
Figure 9A:
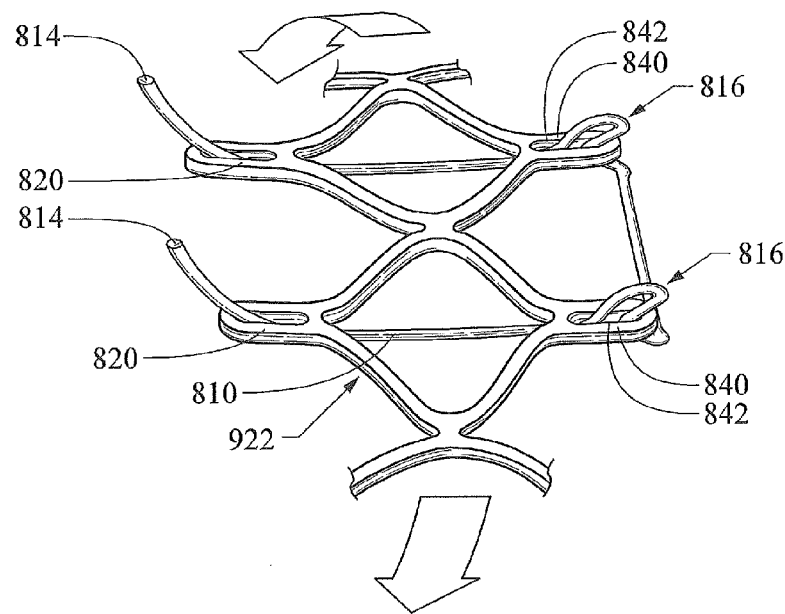
FIG. 9(a) is a plan view of the embodiment of FIG. 8(a) in a fully expanded configuration.
Figure 9B:
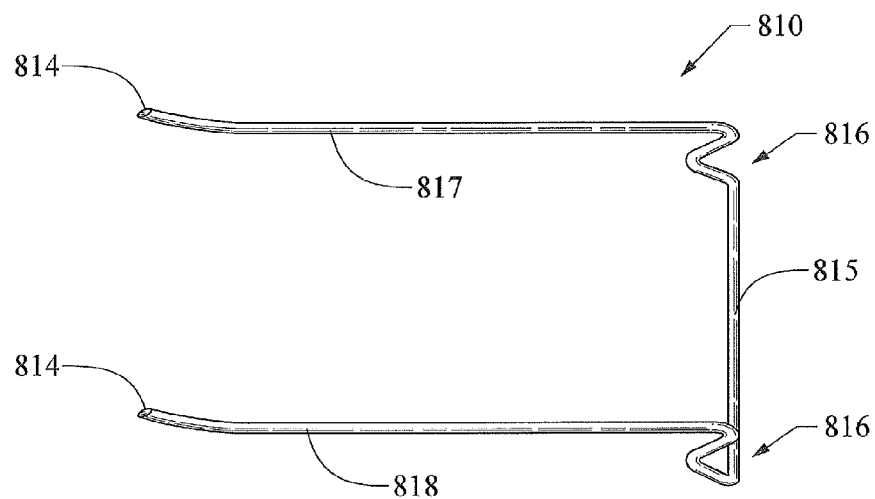
FIG. 9(b) is a plan view of the elongate anchor member of FIG. 9(a) in the fully expanded configuration.
Figure 10A:
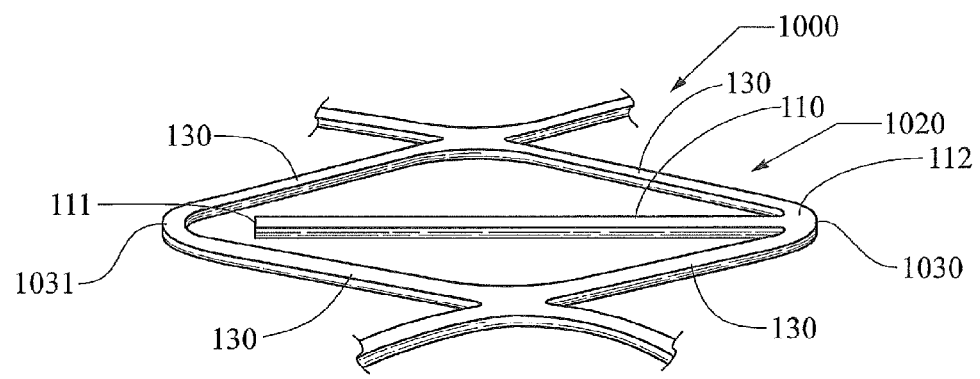
FIGS. 10(a) and (b) illustrate another embodiment of the medical support frame having a retractable anchor member, with the support frame in a collapsed configuration.
Figure 10B:
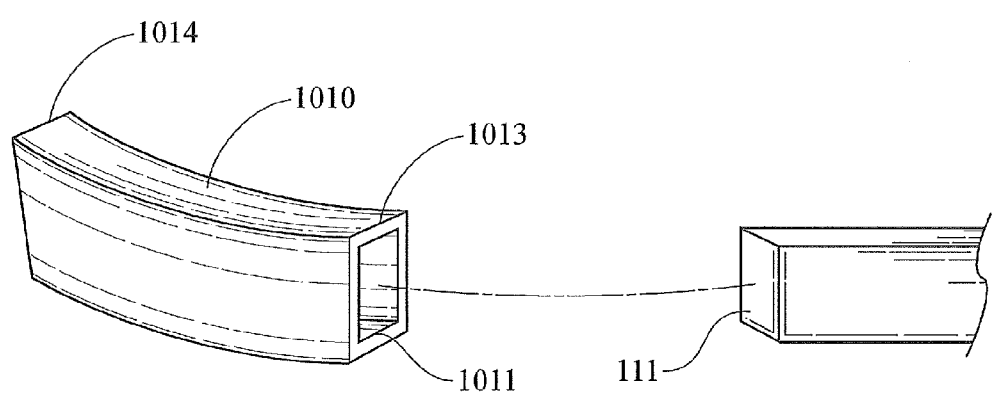
Figure 11A:
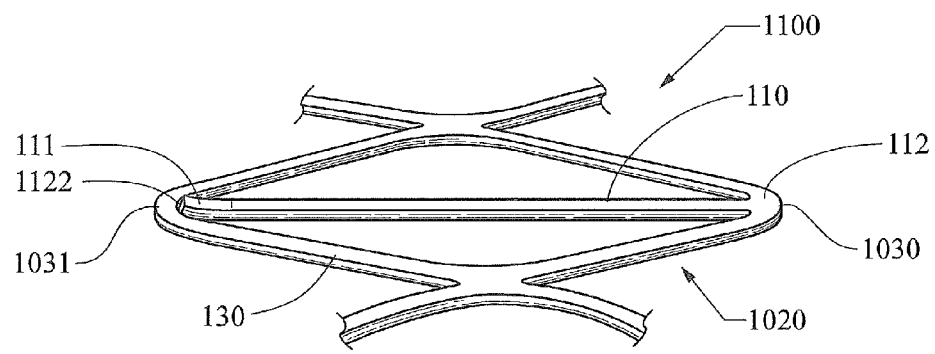
FIGS. 11(a) and (b) illustrate another embodiment of a medical support frame having a retractable anchor member, with the support frame in a collapsed configuration.
Figure 11B:
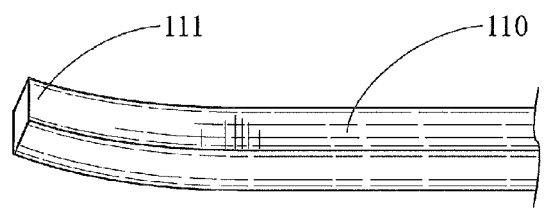
Figure 12A:
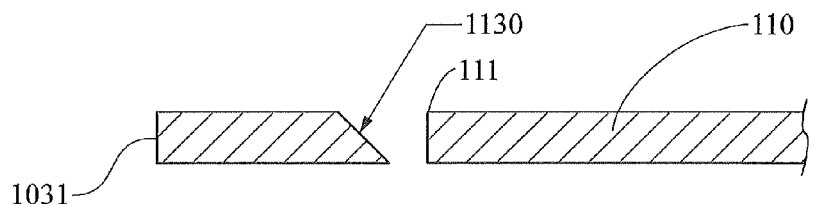
FIGS. 12(a) and (b) are a close-up side cross-sectional views of embodiments of the medical support frames shown in FIGS. 11(a) and (b).
Figure 12B:
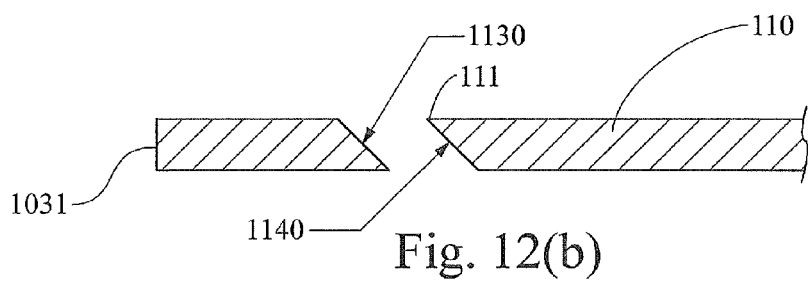

As shown in FIG. 8(b), the elongate anchor member 810 has first and second portions 817, 818 that are configured substantially the same as the elongate member 110 described above in connection with the embodiments of FIGS. 1(a)-(c) and 2(a)-(c). The first and second portions 817, 818 are connected by a member 815 which is expandable in the circumferential direction of the prosthesis. Member 815 includes two straight portions connected at an angle by a bend disposed at a midsection thereof. As the cells 920, 922 expand from the collapsed to the expanded configuration (FIGS. 8(*b*) and 9(*b*)), the expandable member 815 straightens, thereby expanding the elongate anchor member 810. In operation, as the frame 804 is expanded, a distance between the anchor attachment portions 840 and the anchor deployment portions 820 decreases, thereby forcing the engagement ends 814 of the elongate anchor member 810 through the anchor deployment portions 820 in the radially outward direction, as described above in connection with FIGS. 1(*a*)-2(*c*).

FIGS. 10(*a*) and (*b*) illustrate an embodiment of an endoluminal prosthesis 1000 having an elongate member 110 that is integrally formed with the cells 1020 such that the cells 1020 and the elongate member 110 form a single monolithic structure. The elongate member 110 may be integrally formed with the cells 1020 by cutting a cannula or sheet using a laser, water jet, or the like. As shown in FIG. 10(*a*), the elongate member 110 may be formed such that a first end 112 is integrally formed with a bend 1030 joining two circumferentially adjacent strut members 130. The elongate member 110 extends across the cell 1020 in the longitudinal direction from the first end 112 toward the bend 1031 disposed at the opposite side of the cell 1020. In this embodiment, the second end 111 of the elongate member 110 terminates somewhat short of the bend 1031 to allow access to the second end 111. After the cell 1020 and the elongate member(s) 110 have been formed, a barb extension 1010 is attached to the second end 111 of the elongate member 110 in a secondary manufacturing process, as shown in FIG. 10(*b*). The barb extension 1010 may include a receiving feature 1011 disposed at a first end 1013 in the form of a void or the like for receiving the second end 111 of the elongate member 110. The barb extension 1010 may include an angled portion at a second end 1014 that, when attached to the elongate member 110, protrudes in the radially outward direction. The barb extension 1010 may be fixedly attached to the elongate member 110 to prevent relative movement therebetween by, without limitation, press fitting, welding, soldering, adhesives, or the like.

In operation, the elongate member 110 of the endoluminal prosthesis 1000 functions in essentially the same manner as the embodiments described above. That is, as the distance between the bends 1030 and 1031 of the cell 1020 shrinks during radial expansion, the angled face of the barb extension 1010 contacts an inner surface of the bend 1031 and is deflected in a radially outward direction. As the cell 1020 continues to expand the elongate member 110 flexes along its length and extends further in the radially outward direction, thereby creating an anchoring feature.

FIGS. 11(*a*) and 11(*b*) illustrates an alternative embodiment 1100 of the endoluminal prosthesis 1000 of FIGS. 10(*a*) and (*b*), in which the elongate member 110 extends substantially across the entire width of the cell 1020. However, unlike the prosthesis 1000, a barb extension 1010 is not attached to the second end 111 of the elongate member 110. Rather, a portion of the elongate member 110 including the second end 111 is bent in a radially outward direction in a secondary manufacturing process to create an angled portion 1122 similar to the angled portion of the barb extension 1010. This angled portion 1122 of the elongate member 110 and the elongate member 110 itself operate in substantially the same manner as the embodiment 1000 described above, and therefore will not be described again.

In an alternative embodiment, the second end 111 of the elongate member 110 may not be bent to form an angled portion, as shown in FIG. 12(*a*). Instead, a portion of the inner surface of the bend 1031 may be beveled through machining or the like to produce an angled surface 1130. As the width of the cell 1020 decreases during expansion, the angled surface 1130 contacts the second end 111 of the elongate member 110, thereby deflecting the second end 111 in a radially outward direction. Additionally, as shown in the embodiment of FIG. 12(*b*), the second end 111 of the elongate member 110 may also be processed to have an angled face 1140 through machining or the like to help facilitate deflection and ensure the second end 111 of the elongate member 110 does not bind against the angled surface 1130 during expansion of the endoluminal prosthesis. It should be understood that the secondary processing of the bend 1031 illustrated in FIG. 12 may also be applied to the embodiment 1000. Because the embodiments 1000 and 1100 include integrally formed elongate members 110, the overall profile of the resulting endoluminal prostheses may be reduced as compared to the embodiments of FIGS. 1(*a*)-9(*b*) having a separate elongate member.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

The invention claimed is:

1. An implantable medical device comprising:
    a frame having a longitudinal axis, the frame having a collapsed configuration and an expanded configuration, and being configured to move from the collapsed configuration to the expanded configuration;
    an elongate anchor having a first end coupled to the frame and a second movable end that is slidably disposed within a retaining structure on the frame and is longitudinally slideable relative to the frame,
    wherein, when the frame is in the collapsed configuration, the anchor is disposed within the frame; and
    when the frame is in the expanded configuration, at least a portion of the anchor extends out of the frame at an angle to the axis.

2. The implantable medical device of claim 1, wherein when the frame is in the collapsed configuration, the elongate anchor is disposed substantially entirely within a retaining structure of the frame, and as the frame expands from the collapsed configuration to the expanded configuration the length of the portion of the elongate anchor extending out of the retaining structure increases.

3. The implantable medical device of claim 1, wherein the frame includes a deflector that slidably engages the second end of the elongate anchor and forcibly extends the elongate anchor radially outwardly relative to the retaining structure as the frame expands from the collapsed configuration to the expanded configuration.

4. The implantable medical device of claim 1, wherein the first end of the elongate anchor is fixedly attached to the frame.

5. The implantable medical device of claim 1, wherein the first end of the elongate anchor includes an engagement member shaped to engage the retaining structure and to couple the first end to the retaining structure as the frame expands from the collapsed configuration to the expanded configuration.

6. The implantable medical device of claim 1, wherein the retaining structure comprises at least one cell, the cell including a first strut member connected to a second strut member by a first bend, the first and second strut members forming a first angle extending toward a center of the cell, and a third strut member connected to a fourth strut member by a second bend, the third and fourth strut members forming a second angle extending toward the center of the cell, the first and third strut members being connected by a first connecting member and the second and fourth strut members being connected by a second connecting member,
 wherein a longitudinal distance between the first and second bends tends to a maximum when the frame is in the collapsed configuration and tends to a minimum when the frame is in the expanded configuration.

7. The implantable medical device of claim 6, wherein the retaining structure further comprises a deflector connected to the first bend and an elongate anchor receiving portion connected to the second bend,
 wherein, as the frame moves from the collapsed configuration to the expanded configuration, the first end of the elongate anchor is engaged to and restrains the elongate anchor receiving portion of the retaining structure, the second end of the elongate anchor is in sliding contact with the deflector, and the deflector applies a force to the elongate anchor to extend the elongate anchor in a radially outward direction as the distance between the first and second bends decreases.

8. An endoluminal prosthesis comprising:
 a radially expandable frame having a central longitudinally extending frame axis, a first frame location, a second frame location, a collapsed configuration, and an expanded configuration; and
 a barb having a first end coupled to the frame at the first frame location, a second end, and an elongate body extending away from the first frame location toward the second frame location, wherein at least a portion of the barb is slidably disposed within a part of the frame at the second frame location and is longitudinally slideable relative to the frame, and a portion of the barb protrudes from a retaining structure at an angle to the frame axis and forms an anchor when the frame is in the expanded configuration, and
 wherein a distance between the first and second frame locations decreases and a length of the protruding portion of the barb increases as the frame expands from the collapsed configuration to the expanded configuration.

9. The endoluminal prosthesis of claim 8, wherein the elongate body is formed integrally with the frame to form a monolithic structure, and wherein the frame is the retaining structure.

10. The endoluminal prosthesis of claim 8, wherein the first end is fixedly attached to the frame and the second end is free from attachment to the frame, and wherein the barb has a preformed shape such that the barb extends in a radially outward direction as the frame expands from the collapsed configuration to the expanded configuration.

11. The endoluminal prosthesis of claim 8, wherein the retaining structure includes a deflector that slidably engages the second end of the barb and forces the barb to extend in a radially outward direction as the frame expands from the collapsed configuration to the expanded configuration.

12. The endoluminal prosthesis of claim 8, wherein the retaining structure comprises at least one cell, the at least one cell comprising a first strut member connected to a second strut member by a first bend, the first and second strut members forming a first angle extending toward a center of the cell, and a third strut member connected to a fourth strut member by a second bend, the third and fourth strut members forming a second angle opening toward a center of the cell, wherein the first and third strut members are connected by a first connecting member and the second and fourth strut members are connected by a second connecting member,
 wherein the first frame location is disposed at the first bend and the second frame location is disposed at the second bend.

13. An endoluminal prosthesis comprising:
 a radially expandable frame having a central longitudinally extending axis, the frame having a collapsed configuration and an expanded configuration, and being configured to move from the collapsed configuration to the expanded configuration, wherein the frame comprises at least one cell, the cell including a first strut member connected to a second strut member by a first bend, the first and second strut members forming a first angle extending toward a center of the cell, and a third strut member connected to a fourth strut member by a second bend, the third and fourth strut members forming a second angle extending toward a center of the cell, the first and third strut members being connected by a first connecting member and the second and fourth strut members being connected by a second connecting member; and
 a barb member fixedly connected to the frame at the first bend, the barb member having an elongate body extending away from the first bend toward the second bend and is longitudinally slideable relative to the frame,
 wherein, when the frame is in an expanded configuration, a first portion of the elongate body is slidably disposed within the cell,
 and a second portion of the elongate body protrudes radially outward of the cell and forms an anchor,
 wherein a longitudinal distance between the first and second bends decreases and a length of the protruding portion of the elongate body increases as the frame expands from the collapsed configuration to the expanded configuration.

14. The endoluminal prosthesis of claim 13, wherein the cell further comprises a deflector connected to the second bend that slidably engages the first portion of the elongate body and forcibly extends the first portion of the elongate body as the frame expands radially outwardly from the collapsed configuration to the expanded configuration.

15. The endoluminal prosthesis of claim 13, wherein the frame comprises first and second cells.

16. The endoluminal prosthesis of claim 15, wherein the barb member is interengaged with the second bends of the first and second cells such that the barb member is fixedly connected to the frame at the second bends and is in sliding engagement with the first bends of the first and second cells.

17. The endoluminal prosthesis of claim 15, wherein a portion of the barb member extending between the second bends of the first and second cells includes at least two strut members connected by a bend, the at least two strut members flexing relative to each other to expand and compress as the frame expands between the expanded and the collapsed configurations.

18. The endoluminal prosthesis of claim 13, wherein the elongate anchor is formed integrally with the frame to form a monolithic structure.

19. The endoluminal prosthesis of claim 13, wherein a portion of the elongate anchor disposed away from the first bend extends radially outwardly.

20. The endoluminal prosthesis of claim 13, wherein the first end is fixedly attached to the frame and the second end is free from attachment to the frame, and wherein the barb member has a preformed shape such that the barb member extends in a radially outward direction as the frame expands from the collapsed configuration to the expanded configuration.

* * * * *